US012767912B2

(12) United States Patent
Nakai et al.

(10) Patent No.: US 12,767,912 B2
(45) Date of Patent: Oct. 20, 2026

(54) CELL CULTURE DEVICE, CELL CULTURE METHOD, AND PRODUCTION METHOD OF PRODUCT

(71) Applicant: FUJIFILM Corporation, Tokyo (JP)

(72) Inventors: Shinichi Nakai, Kanagawa (JP); Nobuyuki Haraguchi, Kanagawa (JP); Kosuke Taniguchi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 1015 days.

(21) Appl. No.: 17/892,655

(22) Filed: Aug. 22, 2022

(65) Prior Publication Data

US 2022/0403308 A1 Dec. 22, 2022

Related U.S. Application Data

(63) Continuation of application No. PCT/JP2021/006423, filed on Feb. 19, 2021.

(30) Foreign Application Priority Data

Mar. 18, 2020 (JP) ................................ 2020-048440

(51) Int. Cl.
*C12M 3/02* (2006.01)
*B01F 27/80* (2022.01)
(Continued)

(52) U.S. Cl.
CPC ............... *C12M 3/02* (2013.01); *B01F 27/80* (2022.01); *C07K 16/00* (2013.01); *C12M 27/02* (2013.01); *C12N 5/06* (2013.01)

(58) Field of Classification Search
None
See application file for complete search history.

(56) References Cited

U.S. PATENT DOCUMENTS

2006/0216818 A1 9/2006 Amano
2007/0065312 A1* 3/2007 Whitehouse ............. B67D 1/10 417/420

(Continued)

FOREIGN PATENT DOCUMENTS

EP 2 860 240 A1 4/2015
GB 2185862 A * 7/1987 ............... H02K 7/20

(Continued)

OTHER PUBLICATIONS

Japanese Office Action for corresponding Japanese Application No. 2022-508155, dated Jan. 23, 2024, with English translation.

(Continued)

*Primary Examiner* — William H. Beisner
(74) *Attorney, Agent, or Firm* — Birch, Stewart, Kolasch & Birch, LLP

(57) ABSTRACT

A cell culture device (1) includes: a culture vessel (10) that accommodates a cell suspension containing cells and a culture medium; and a stirring device (30) that is provided at a bottom part of the culture vessel (10) to stir the cell suspension accommodated in the culture vessel (10). The stirring device (30) has a shaft part (32), and a rotating part (33) rotatable with the shaft part (32) as a rotation axis. The rotating part (33) has a hole part (36) into which the shaft part (32) is inserted, and a gap (37) of 100 μm or more is secured between an interior wall demarcating the hole part (36) and the shaft part (32). A closing part (38) that closes an end part of the gap (37) in an axial direction of the rotation axis is provided.

14 Claims, 6 Drawing Sheets

(51) Int. Cl.

| | |
|---|---|
| ***C07K 16/00*** | (2006.01) |
| ***C12M 1/06*** | (2006.01) |
| ***C12N 5/07*** | (2010.01) |

(56) References Cited

U.S. PATENT DOCUMENTS

| | | | | |
|---|---|---|---|---|
| 2010/0197003 | A1 | 8/2010 | Terentiev et al. | |
| 2014/0349385 | A1 | 11/2014 | Erdenberger et al. | |
| 2015/0151261 | A1 | 6/2015 | Isailovic | |
| 2015/0165399 | A1 | 6/2015 | Rawlings | |
| 2015/0252315 | A1 | 9/2015 | Wada et al. | |
| 2018/0155667 | A1* | 6/2018 | Stobbe | C12M 47/10 |
| 2020/0399585 | A1 | 12/2020 | Takahashi et al. | |

FOREIGN PATENT DOCUMENTS

| | | | | |
|---|---|---|---|---|
| GB | 2196800 | A * | 5/1988 | B01F 33/453 |
| JP | 2006-296423 | A | 11/2006 | |
| JP | 2007-522801 | A | 8/2007 | |
| JP | 2015-110223 | A | 6/2015 | |
| JP | 2015-147206 | A | 8/2015 | |
| JP | 2017-51947 | A | 3/2017 | |
| JP | 2018-50550 | A | 4/2018 | |
| WO | WO 2013/187359 | A1 | 12/2013 | |
| WO | WO-2014180954 | A1 * | 11/2014 | F16C 32/0402 |
| WO | WO 2019/181234 | A1 | 9/2019 | |

OTHER PUBLICATIONS

International Preliminary Report on Patentability and Written Opinion of the International Searching Authority (Forms PCT/IB/326, PCT/IB/373, and PCT/ISA/237) for International Application No. PCT/JP2021/006423, dated Sep. 29, 2022, with an English translation.

International Search Report (Form PCT/ISA/210) for International Application No. PCT/JP2021/006423, dated May 11, 2021, with an English translation.

Extended European Search Report for corresponding European Application No. 21771343.7, dated Jul. 14, 2023.

Japanese Notice of Reasons for Refusal for corresponding Japanese Application No. 2022-508155, dated Aug. 22, 2023, with an English translation.

* cited by examiner

CELL CULTURE DEVICE, CELL CULTURE METHOD, AND PRODUCTION METHOD OF PRODUCT

This application is a continuation application of International Application No. PCT/JP2021/006423, filed Feb. 19, 2021, the disclosure of which is incorporated herein by reference in its entirety. Further, this application claims priority from Japanese Patent Application No. 2020-048440 filed on Mar. 18, 2020, the disclosures of which is incorporated herein by reference in its entirety.

BACKGROUND

1. Technical Field

The disclosed technology relates to a cell culture device, a cell culture method, and a production method of a product.

2. Description of the Related Art

As technologies relating to a stirring device used for stirring cell suspensions, the following technology is known. For example, JP2015-147206A discloses a stirrer comprising an impeller attached to a rotating shaft, and a housing assembly. The housing assembly comprises an upper seal assembly and a lower seal assembly. The upper seal assembly and the lower seal assembly each have a central channel for receiving the rotating shaft, and include a seal having a cyclic opening portion.

SUMMARY

In a large-scale culture in which a large amount (for example, 10 L or more) of a cell suspension is accommodated in a culture vessel and cultured, a stirring culture in which the cells are cultured while stirring the cell suspension is generally applied. Stirring of the cell suspension promotes the supply of oxygen and nutrients to the cells. For stirring the cell suspension, a stirring device having a rotating stirring blade is used. However, in a case where such a stirring device is used, the cells may be damaged by the shear generated by the stirring, which may cause problems such as a decrease in the cell proliferation rate and a decrease in the viability.

The disclosed technology has been made in view of the above-mentioned points, and an object thereof is to inhibit damage to cells caused by stirring a cell suspension.

A cell culture device according to the disclosed technology includes: a culture vessel that accommodates a cell suspension containing cells and a culture medium; and a stirring device that is provided at a bottom part of the culture vessel to stir the cell suspension accommodated in the culture vessel. The stirring device has a shaft part; a rotating part that has a hole part into which the shaft part is inserted, and is provided to have a gap of 100 μm or more between an interior wall demarcating the hole part and the shaft part so that the rotation part is rotatable with the shaft part as a rotation axis; and a closing part that closes an end part of the gap in an axial direction of the rotation axis.

A dimension of the gap is preferably 400 μm or less. The closing part may be provided at one end part of the gap in the axial direction of the rotation axis, or may be provided at both end parts of the gap in the axial direction of the rotation axis. The rotating part may be rotated by a magnetic force. The closing part may be configured to have a packing made of polymer. The culture vessel may have the form of a bag.

A cell culture method according to the disclosed technology is a cell culture method which uses the above-mentioned cell culture device, the method including culturing cells while stirring a cell suspension accommodated in a culture vessel by rotation of a rotating part.

The cells are preferably cultured at a shear rate $\gamma$ [$sec^{-1}$] defined by Equation (I) in a range of 200 $sec^{-1}$ or more and 3200 $sec^{-1}$ or less, in a case where a dimension of a gap is t [μm], and a rotation rate of the rotating part is s [m/sec].

$$\gamma = s/t \times 10^{-6} \quad \text{(I)}$$

The culture scheme may be a perfusion culture scheme, or may be a fed-batch scheme. The cells to be cultured may be Chinese Hamster Ovary (CHO) cells.

A production method of a product according to the disclosed technology is a production method of a product which is for producing a product produced from cells cultured by the above-mentioned cell culture method, the method including a step of collecting a culture medium containing the product from a culture vessel. The product may be an antibody.

According to the disclosed technology, the damage to cells caused by stirring a cell suspension can be inhibited.

BRIEF DESCRIPTION OF THE DRAWINGS

Exemplary embodiments according to the technique of the present disclosure will be described in detail based on the following figures, wherein.

DETAILED DESCRIPTION

Figure 1:
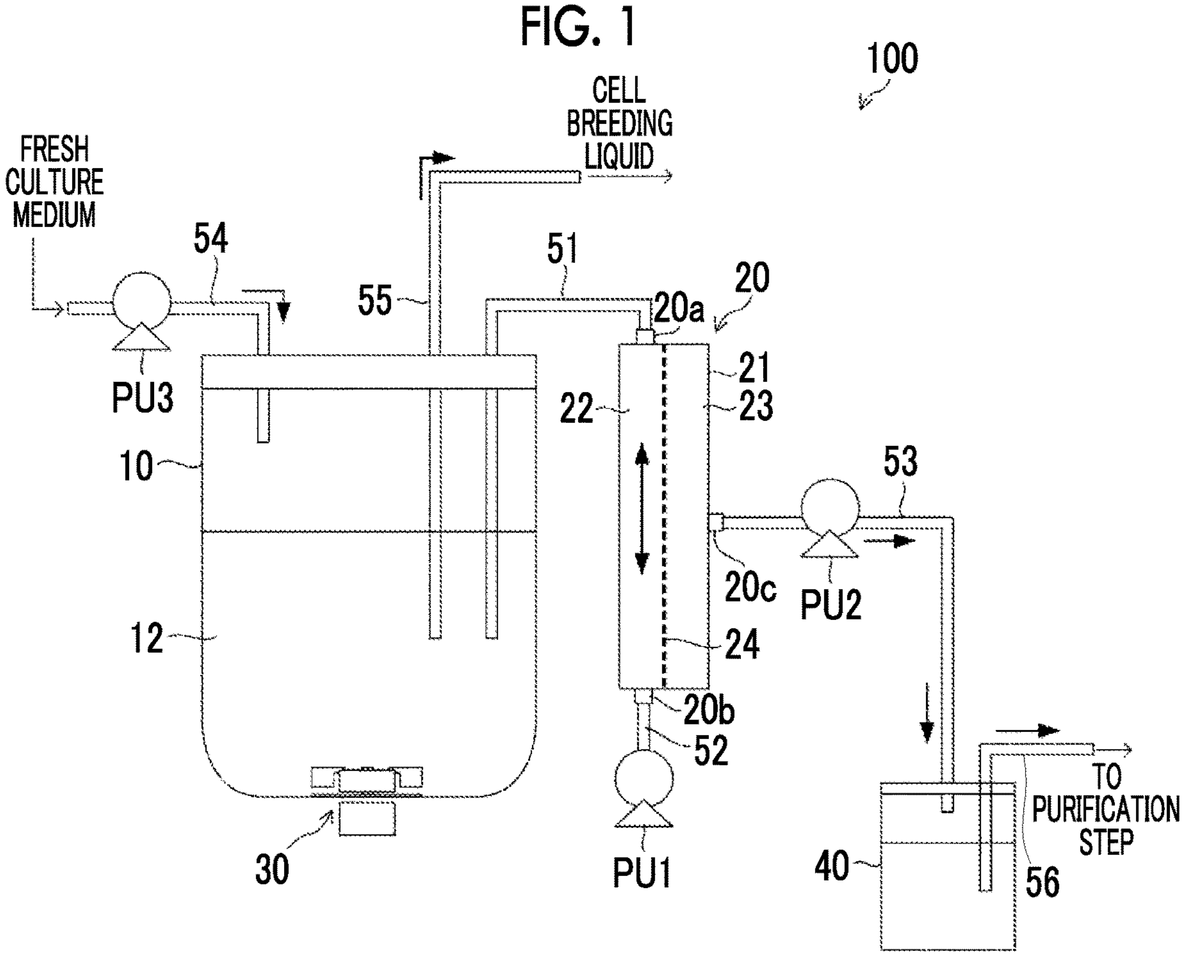
FIG. 1 is a view showing an example of the configuration of a cell culture device according to the embodiment of the disclosed technology.

Hereinafter, an example of the embodiment of the present invention will be described with reference to the drawings.

In the respective drawings, the same or equivalent components and portions are denoted by the same reference numerals, and redundant description will be omitted as appropriate.

FIG. 1 is a view showing an example of the configuration of a cell culture device 100 according to the embodiment of the disclosed technology. The cell culture device 100 includes a culture vessel 10 accommodating a cell suspension 12 containing cells and a culture medium; a filter unit 20 having a filter membrane 24 that applies a membrane separation treatment to the cell suspension extracted from the culture vessel 10; a flow channel 51 through which the cell suspension moving between the filter unit 20 and the culture vessel 10 passes; a flow channel 53 through which components that have permeated through the filter membrane 24 passes; and a collecting tank 40 connected to the flow channel 53. The cell culture device 100 can be suitably used for cell culture by a perfusion culture scheme in which a fresh culture medium is continuously supplied to the culture vessel 10 while a culture medium containing a product such as an antibody is continuously extracted from the culture vessel 10.

The form of the culture vessel 10 is not particularly limited, but a bag type having the capacity of, for example, 10 L or more, which is used for mass culture of cells, can be preferably used. At the bottom part of the culture vessel 10, a stirring device 30 is provided for stirring the cell suspension contained in the culture vessel 10. The detailed configuration of the stirring device 30 will be described later.

One end of the flow channel 51 is inserted into the cell suspension 12, and the other end is connected to a flow port 20*a* of the filter unit 20.

The filter unit 20 includes a vessel 21; and a filter membrane 24 that partitions the space inside the vessel 21 into a supply side 22 and a permeation side 23 and applies a membrane separation treatment to the cell suspension 12 extracted from the culture vessel 10. Furthermore, on the supply side 22, the filter unit 20 has flow ports 20*a* and 20*b* through which the cell suspension 12 flows. The cell suspension 12 extracted from the culture vessel 10 flows into the inside of the vessel 21 from the flow port 20*a* and passes through the filter membrane 24 until reaching the flow port 20*b*. The filter unit 20 performs a membrane separation treatment by a tangential flow method of pouring a liquid as an object of the membrane separation treatment so as to cause the liquid to flow along the membrane surface of a filter membrane 24 (in a direction parallel to the membrane surface) and sending small-sized components toward the permeation side 23.

One end of the flow channel 52 is connected to the flow port 20*b*, and the other end of the flow channel 52 is connected to a pump PU1. The pump PU1 is a diaphragm pump, for example, and by operating the pump PU1, the cell suspension 12 extracted from the culture vessel 10 forms a reciprocating flow along the membrane surface of the filter membrane 24. Although not shown in the drawing, for example, by providing a separate flow channel between the culture vessel 10 and the filter unit, the flow channel can be configured such that the cell suspension 12 extracted from the culture vessel 10 forms a flow that circulates in one direction along the membrane surface of the filter membrane 24.

The cells contained in the cell suspension 12 do not permeate through the filter membrane 24, but are returned to the culture vessel 10 via the flow channel 51. On the other hand, the product such as antibodies contained in the cell suspension 12 permeates through the filter membrane 24, and is discharged to the outside of the vessel 21 through a discharge port 20*c* provided on the permeation side 23. On the permeation side 23, the flow channel 53 provided with a pump PU2 is connected, and a permeation liquid containing the product such as antibodies which has permeated through the permeation side 23 is collected in the collecting tank 40 via the flow channel 53.

Furthermore, a hollow fiber membrane can be used as the filter membrane 24. By using a hollow fiber membrane, a risk of cells permeating into the permeation side can be reduced, as compared to the case of using a mesh filter. Also, a risk of the occurrence of clogging caused by cells infiltrating into the filter membrane 24 can be reduced. Thereby, loss of cells can be reduced.

The product such as antibodies contained in the permeation liquid that has permeated through the filter membrane 24 and collected in the collecting tank 40 is sent, via a flow channel 56, to a purification treatment unit (not shown in the drawing) in which purification of antibodies is performed. The cell culture device 100 has a flow channel 54 for supplying a fresh culture medium to the culture vessel 10; and a pump PU3 provided in the middle of the flow channel 54. In order to prevent the concentration of cells in the culture vessel 10 from excessively increasing, a cell bleeding treatment of taking out a portion of cells inside the culture vessel 10 at an appropriate timing during the culture period is carried out. During the cell bleeding treatment, the cells in the culture vessel 10 are discharged to the outside of the culture vessel 10 via a flow channel 55.

The cell culture device 100 shown in FIG. 1 performs a separation treatment by means of the membrane separation treatment using the filter unit 20; however, it is also possible to replace the filter unit 20 with a treatment unit of performing a separation treatment according to a sonic agglomeration method.

Figure 2A:
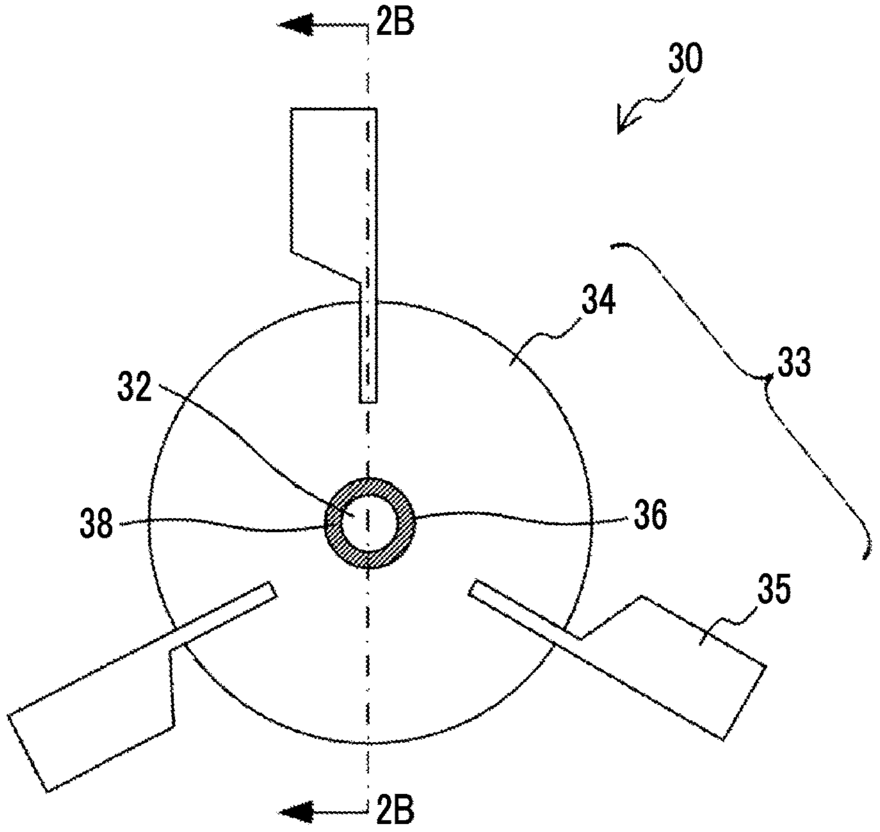
FIG. 2A is a plan view showing an example of the configuration of a stirring device according to the embodiment of the disclosed technology.
Figure 2B:
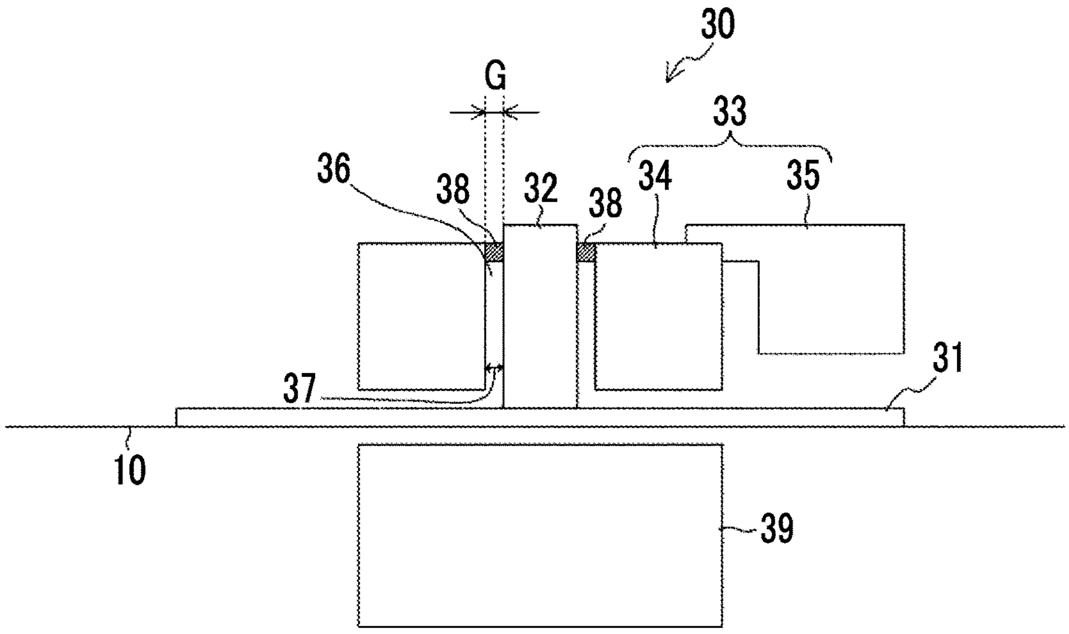
FIG. 2B is a cross-sectional view taken along the line 2B-2B in FIG. 2A.

FIG. 2A is a plan view showing an example of the configuration of the stirring device 30. FIG. 2B is a cross-sectional view taken along the line 2B-2B in FIG. 2A.

The stirring device 30 has a pedestal part 31, a shaft part 32, and a rotating part 33. The pedestal part 31 is a plate-shaped member, and is fixed to the bottom surface of the culture vessel 10. The shaft part 32 is a cylindrical member extending in the direction perpendicular to the surface of the pedestal part 31. The shaft part 32 may be configured integrally with the pedestal part 31, or may be configured as a separate body from the pedestal part 31.

The rotating part 33 has a main body 34 and a leaf blade part 35. The main body 34 has a cylindrical shape having the height as high as the length of the shaft part 32 in the axial direction. The main body 34 has a hole part 36 penetrating the main body 34 in the center thereof. The shaft part 32 is inserted into the hole part 36. The main body 34 can rotate with the shaft part 32 as a rotation axis. A gap (clearance) 37 is secured between the inner wall on the hole part side of the main body (the inner wall demarcating the hole part 36) and the shaft part 32. That is, the rotating part 33 is not in contact with the shaft part 32.

The main body 34 is provided with three leaf blade parts 35. The leaf blade part 35 has a portion protruding from the outer edge of the main body 34, and functions as a stirring blade for stirring the cell suspension 12 by rotating with the main body 34. Stirring of the cell suspension 12 promotes the supply of oxygen and nutrients to the cells. The shape of the leaf blade part 35 is not particularly limited, and may be any shape that promotes stirring. The leaf blade part 35 may be configured integrally with the main body 34, or may be configured as a separate body from the main body 34.

Furthermore, the number of the leaf blade parts 35 may be two or less, or may be four or more.

The stirring device 30 has a closing part 38 that closes the upper end part of the gap 37 in the axial direction of the rotation axis. The closing part 38 has the form of a ring shape corresponding to the shape seen from the upper side of the gap 37 in the axial direction. The surface of the closing part 38 in contact with the shaft part 32 may be adhered to the shaft part 32. In this case, the surface of the closing part 38 in contact with the inner wall on the hole part side of the main body 34 is slidable with respect to the inner wall on the hole part side of the main body 34. On the other hand, the surface of the closing part 38 in contact with the inner wall on the hole part side of the main body 34 may be adhered to the inner wall on the hole part side of the main body 34. In this case, the surface of the closing part 38 in contact with the shaft part 32 is slidable with respect to the shaft part 32. A packing made of polymer can be suitably used as the closing part 38. During the culture period, the stirring device 30 is in a state of being immersed in the cell suspension 12. In a case where the closing part 38 closes the end part of the gap 37, the inflow of the cell suspension 12 into the gap 37 can be inhibited. The closing part 38 serves as resistance to the rotation of the rotating part 33, but the contact pressure of the sliding surface is adjusted to such an extent that the rotation of the rotating part 33 is not hindered.

Figure 3A:
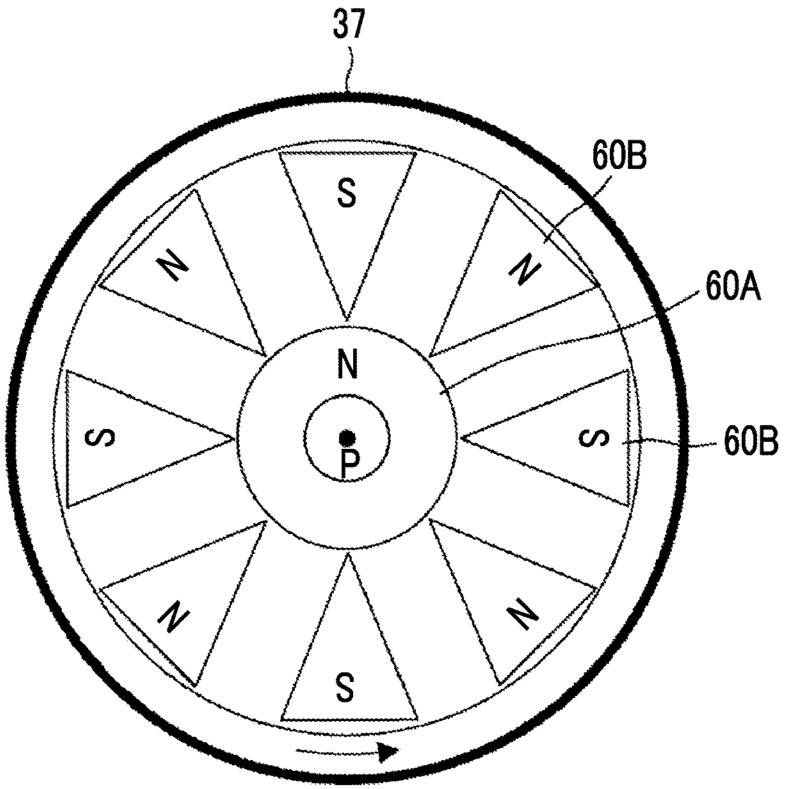
FIG. 3A is a view showing an example of the internal configuration of a driving unit according to the embodiment of the disclosed technology.

The rotating part 33 is rotated by a magnetic force. On the outside of the culture vessel 10, the stirring device 30 has a driving unit 39 installed near the rotating part 33. FIG. 3A is a view showing an example of the internal configuration of the driving unit 39. The driving unit 39 has a circular surface facing the bottom surface of the rotating part 33, and a center point P of this circle is aligned with the position (that is, the rotation axis of the rotating part 33) corresponding to the shaft part 32. The driving unit 39 has a ring-shaped magnet 60A having a center point at the center point P, and a plurality of magnets 60B disposed radially around the center point P. The plurality of magnets 60B are disposed such that the polarities on the side facing the rotating part 33 are alternately reversed. The plurality of magnets 60B are rotated around the center point P by a motor mechanism (not shown in the drawing).

Figure 3B:
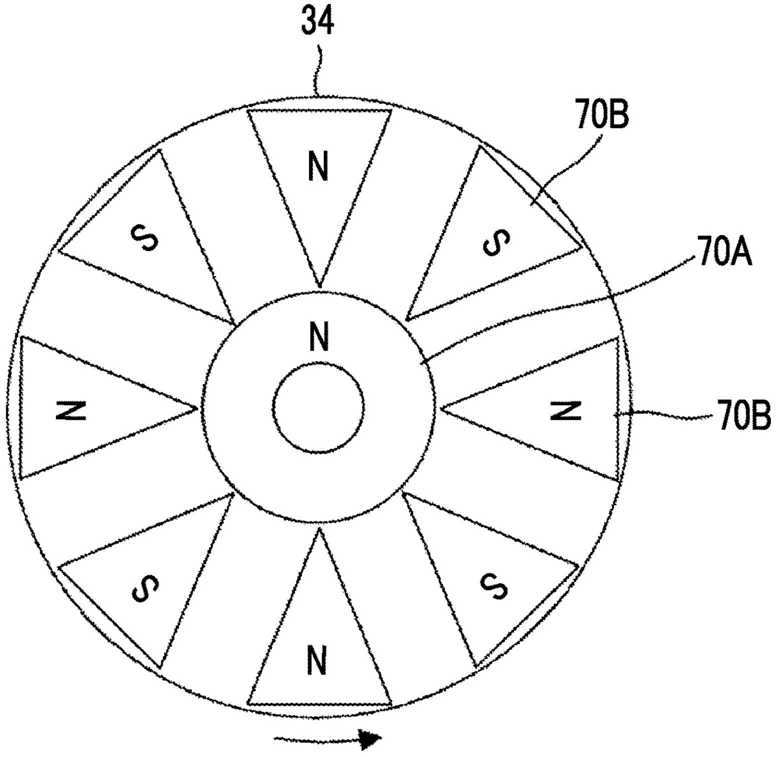
FIG. 3B is a view showing an example of the internal configuration of a main body of a rotating part according to the embodiment of the disclosed technology.

FIG. 3B is a view showing an example of the internal configuration of the main body 34 of the rotating part 33. The rotating part 33 has a ring-shaped magnet 70A and a plurality of magnets 70B which are configured in the same manner as the driving unit 39. The magnet 70A is disposed at the position corresponding to the magnet 60A of the driving unit 39, and the plurality of magnets 70B are disposed at the position corresponding to the plurality of magnets 60B of the driving unit 39. The magnet 60A and the magnet 70A have the same polarity on the opposite sides (N pole in the present embodiment). Accordingly, repulsive forces act on the magnet 60A and the magnet 70A. Due to this repulsive force, the rotating part 33 rises from the pedestal part 31. Furthermore, a force attracting each other acts on the magnet 60B and the magnet 70B. Therefore, with the rotation of the magnet 60B of the driving unit 39, the rotating part 33 rotates with the shaft part 32 as the rotation axis in a state of being levitated from the pedestal part 31.

Here, in a case where the dimension of the gap 37 is t [μm] and the rotation rate of the rotating part 33 is s [m/sec], the shear rate γ [$sec^{-1}$] acting on the cell suspension 12 that has flowed into the gap 37 by the rotation of the rotating part 33 is expressed by Equation (1).

$$\gamma = s/t \times 10^{-6} \qquad (1)$$

During the culture period, the shear rate γ is preferably 200 $sec^{-1}$ or more and 3200 $sec^{-1}$ or less, more preferably 500 $sec^{-1}$ or more and 2500 $sec^{-1}$ or less, and most preferably 600 $sec^{-1}$ or more and 2000 $sec^{-1}$ or less. By setting the shear rate γ to 200 $sec^{-1}$ or more, stirring of the cell suspension 12 is promoted, which makes it possible to inhibit cell precipitation and cell choking due to insufficient oxygen supply. By setting the shear rate γ to 3200 $sec^{-1}$ or less, the shear acting on the cells contained in the cell suspension 12 that has flowed into the gap 37 can be inhibited. Accordingly, damage to the cells due to stirring can be inhibited, making it possible to inhibit a deterioration of cell proliferation and viability.

Furthermore, the dimension of the gap 37 (that is, the distance between the surface of the shaft part 32 and the inner wall of the hole part 36) G is preferably 100 μm or more and 400 μm or less, more preferably 100 μm or more and 300 μm or less, and most preferably 120 μm or more and 200 μm or less. By setting the dimension G of the gap 37 to 100 μm or more, the shearing acting on the cells contained in the cell suspension that has flowed into the gap 37 can be inhibited. By setting the dimension G of the gap 37 to 400 μm or less, the eccentricity of the rotating part 33 with respect to the shaft part 32 can be inhibited. Accordingly, an increase in the shear rate due to eccentricity can be inhibited, making it possible to inhibit damage to cells due to shearing. In addition, wear of the shaft part 32 due to eccentricity can be inhibited.

The dimension G can be calculated by (the inner diameter of the main body of the rotating part)/2−(the diameter of the shaft part)/2.

Here, in a stirring culture in which a cell suspension is stirred using a rotating stirring blade, it is generally known that the shear generated at the distal end of the stirring blade is a factor of the damage to cells. The inventors of the present invention have found that not only the distal end of the stirring blade but also the shear generated in the gap 37 formed around the rotation axis of the stirring blade is also a factor of the damage.

The stirring device 30 according to the embodiment of the disclosed technology has the closing part 38 that closes the end part, in the axial direction of the rotation axis, of the gap 37 formed between the inner wall on the hole part side of the main body 34 and the shaft part 32. Accordingly, the inflow of the cell suspension 12 into the gap 37 can be inhibited. Therefore, the number of cells damaged by the shear generated in the gap 37 can be reduced. Furthermore, by setting the dimension G of the gap 37 to 100 μm or more, even in a case where the cell suspension 12 flows into the gap 37, the damage to the cells due to the shear generated in the gap 37 can be inhibited.

Figure 4A:
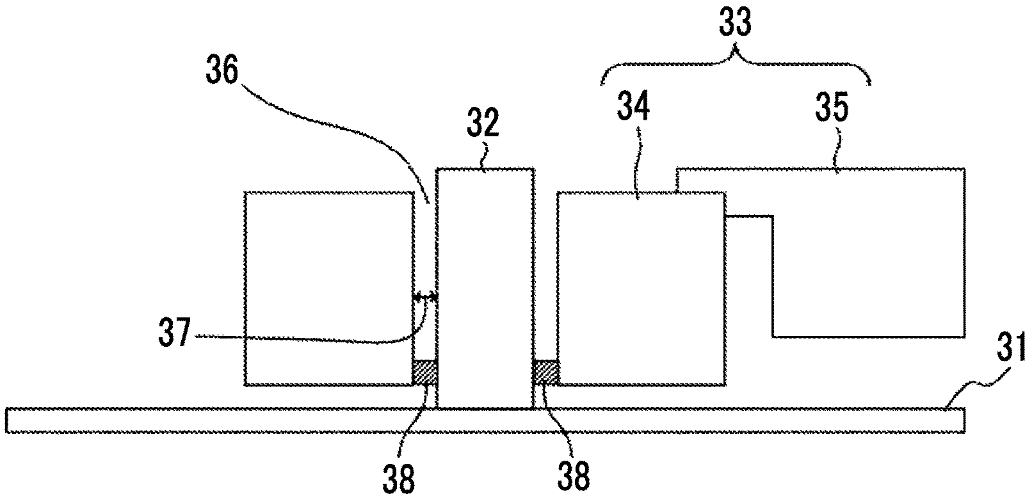
FIG. 4A is a view showing another example of the configuration of a closing part according to the embodiment of the disclosed technology.
Figure 4B:
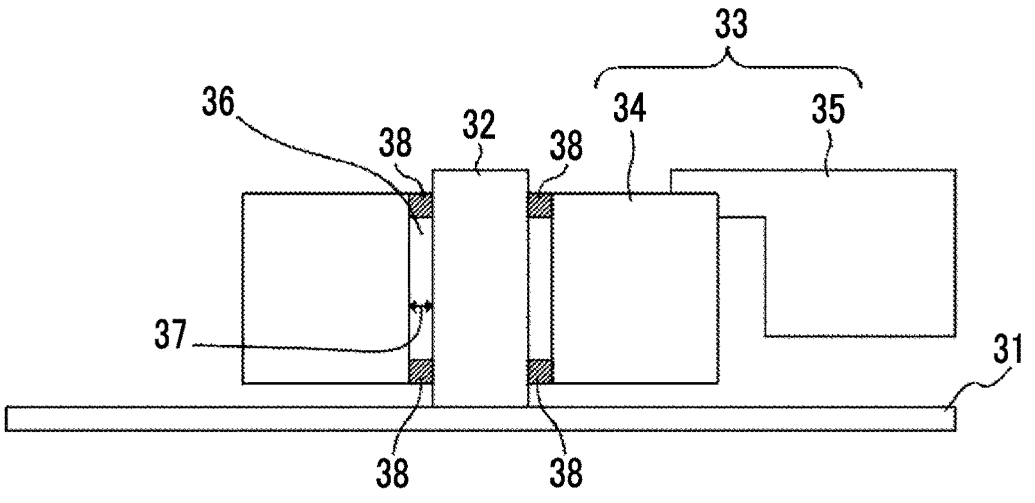
FIG. 4B is a view showing still another example of the configuration of the closing part according to the embodiment of the disclosed technology.
Figure 4C:
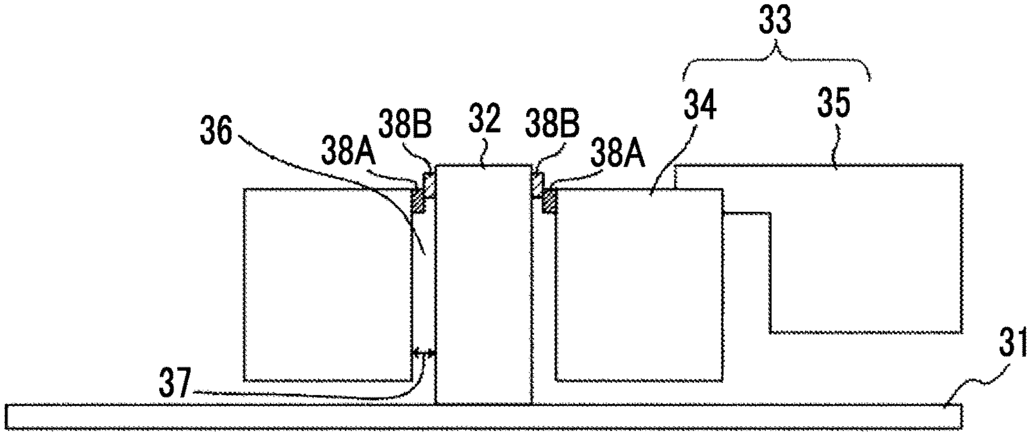
FIG. 4C is a view showing still another example of the configuration of the closing part according to the embodiment of the disclosed technology.

FIG. 4A to FIG. 4C are cross-sectional views showing another example of the configuration of the closing part 38. As shown in FIG. 4A, the closing part 38 may be configured to close the lower end part of the gap 37 in the axial direction of the rotation axis. The inflow of the cell suspension 12 into the gap 37 can be inhibited also by closing the lower end part of the gap 37 as above.

Furthermore, as shown in FIG. 4B, the closing part 38 may be configured to close both end parts of the gap 37 in the axial direction of the rotation axis. This makes it possible to substantially and completely prevent the inflow of the cell suspension 12 into the gap 37.

Furthermore, as shown in FIG. 4C, closing of the end part of the gap 37 in the axial direction of the rotation axis may be performed by the closing parts 38A and 38B. The closing part 38A is attached to the inner wall of the hole part 36, and the closing part 38B is attached to the surface of the shaft part 32. The closing part 38A and the closing part 38B are disposed at positions where their sliding surfaces are in contact with each other. By closing the end parts of the gap 37 with the closing parts 38A and 38B that are in contact with each other as above, the sealing property of the gap 37 can be improved.

Figure 5:
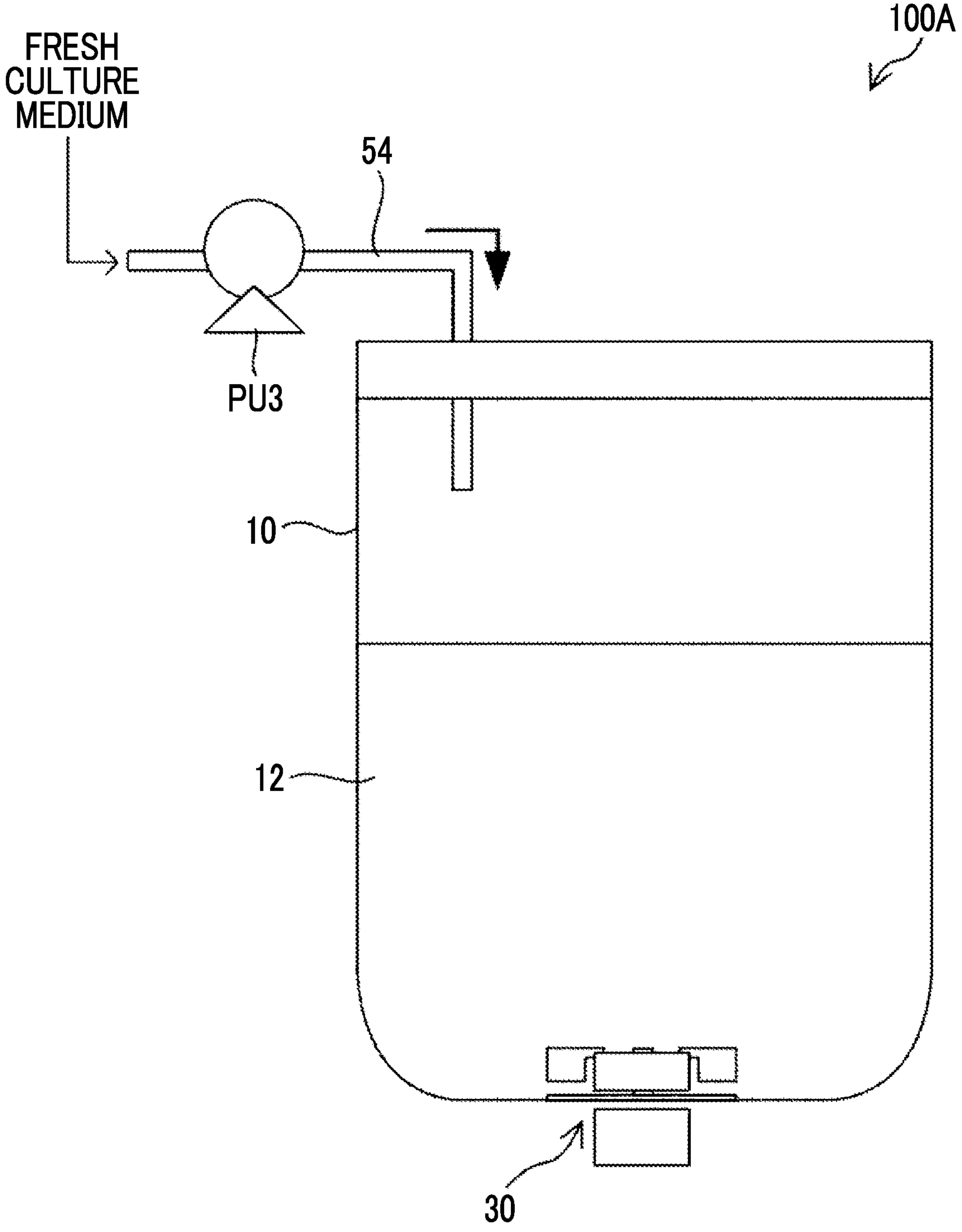
FIG. 5 is a view showing another example of the configuration of the cell culture device according to the embodiment of the disclosed technology.

FIG. 5 is a view showing an example of the configuration of a cell culture device 100A according to another embodiment of the disclosed technology. The cell culture device 100A is configured to include a culture vessel 10, a stirring device 30, a flow channel 54, and a pump PU3. The cell culture device 100A does not include the filter unit 20, the collecting tank 40, and the flow channel 55 for performing the cell bleeding treatment, which are provided in the cell culture device 100 shown in FIG. 1. The cell culture device 100A can be suitably used for cell culture by the fed-batch scheme. The cell culture by the fed-batch scheme is a scheme in which a fresh culture medium is added to the culture vessel 10 at a predetermined timing without extracting the cell suspension 12 accommodated in the culture vessel 10 during the culture period. Even in the case of performing the cell culture by the fed-batch scheme, by providing the stirring device 30 to which the disclosed technology has been applied, the damage to cells due to stirring of the cell suspension 12 can be inhibited.

A cell culture method according to the embodiment of the disclosed technology uses the cell culture device 100 (refer to FIG. 1) or 100A (refer to FIG. 5), in which culture of cells is performed while stirring the cell suspension 12 accommodated in the culture vessel 10 by rotating the rotating part 33 of the stirring device 30. By using the cell culture device 100 (refer to FIG. 1), cell culture by the perfusion culture scheme can be performed. By using the cell culture device 100A (refer to FIG. 5), cell culture by the fed-batch scheme can be performed.

The cells cultured using the cell culture device 100 or the cell culture device 100A are not particularly limited, but are preferably cells that produce a product. The cells used as the cells that produce a product are not particularly limited; however, examples include eukaryotic cells such as animal cells, plant cells, and yeasts; prokaryotic cells such as Bacillus subtilis; and Escherichia coli. Animal cells such as CHO cells, BHK-21 cells, and SP2/0-Ag14 cells are preferred, and CHO cells are more preferred. Furthermore, the product produced from the cells is not particularly limited as long as it is a substance that the above-mentioned cells produce in the culture medium, and examples thereof alcohols, enzymes, antibiotic substances, recombinant proteins, and antibodies, where recombinant proteins and antibodies are preferable, and antibodies are more preferable.

An antibody produced by an animal cell is not particularly limited; however, examples include an anti-IL-6 receptor antibody, an anti-IL-6 antibody, an anti-glypican-3 antibody, an anti-CD3 antibody, an anti-CD20 antibody, an anti-GPIIb/IIIa antibody, an anti-TNF antibody, an anti-CD25 antibody, an anti-EGFR antibody, an anti-Her2/neu antibody, an anti-RSV antibody, an anti-CD33 antibody, an anti-CD52 antibody, an anti-IgE antibody, an anti-CD11a antibody, an anti-VEGF antibody, and an anti-VLA4 antibody. Examples of the antibodies include monoclonal antibodies derived from animals such as human being, mouse, rat, hamster, rabbit, and monkey, as well as artificially modified antibodies such as a chimeric antibody, a humanized antibody, and a bispecific antibody.

By rotating the rotating part 33 of the stirring device 30 during the culture period, stirring of the cell suspension 12 is promoted, which promotes the supply of oxygen and nutrients to the cells. Regarding the rotation rate s of the rotating part 33, the rotation rate of the rotating part 33 is preferably controlled such that the shear rate γdefined by Equation (1) is 200 $sec^{-1}$ or more and 3200 $sec^{-1}$ or less. The rotation rate of the rotating part 33 may be constant, or may be changed according to the culture state such as cell density or the elapsed time from the start of culture.

A production method of a product according to the embodiment of the disclosed technology is a method of producing a product produced from the cells cultured by the above-mentioned culture method, the production method including a step of collecting a culture medium containing the product from the culture vessel 10. The product is preferably an antibody. By culturing, for example, CHO cells in the culture vessel 10, an antibody produced from the CHO cells can be obtained.

In a case where the cell culture device 100 shown in FIG. 1 is used, the product such as antibodies can be collected in the collecting tank 40. In a case where the cell culture device 100A shown in FIG. 5 is used, the product such as antibodies can be collected together with the cell suspension 12 accommodated in the culture vessel 10.

The antibody thus obtained or a fragment thereof can be purified until the antibody or the fragment becomes approximately uniform. Separation and purification of the antibody or a fragment thereof may be carried out using conventional separation and purification methods used for general polypeptides. For example, in a case in which a column for chromatography such as affinity chromatography, a filter, ultrafiltration, salting out, dialysis, SDS polyacrylamide gel electrophoresis, and isoelectric point electrophoresis are selected as appropriate and combined, the antibody can be separated and purified; however, the methods are not limited to these. Measurement of the concentration of the antibody thus obtained can be carried out by measurement of the absorbance, an enzyme-linked immunosorbent assay (ELISA), or the like.

EXAMPLE

Cell culture was performed by the perfusion culture scheme using the cell culture device 100 having the configuration shown in FIG. 1. CHO cells were used as cells to be cultured. As the culture vessel 10, a single-use bag-type vessel having the capacity of 10 L was used. The seeding density of the cells was $3\times10^5$ cells/mL. The supply of a fresh culture medium and the extraction of the cell suspension from the culture vessel 10 were performed after the third day from the start of the culture. Cell bleeding treatment was appropriately performed so that the cell density was maintained at about $110\times10^6$ cells/ml during the culture period. The rotation rate of the rotating part 33 of the stirring device 30 was set to 200 rpm from the start of the culture to the 10th day, and 240 rpm after the 10th day. During the culture period, air having the flow rate of 0.1 L/min was supplied from the upper surface in the culture vessel 10. Pure oxygen was supplied from a 20 μm sparger disposed at the bottom part of the culture vessel 10 so that the oxygen concentration in the cell suspension in the culture vessel 10 was 33%.

As a stirring device for stirring the cell suspension, the one in Table 1 below was used. That is, as the stirring device according to the embodiment of the disclosed technology, a stirring device which had a closing part having the configuration shown in FIG. 4C and in which the dimension G of the gap 37 was 150 μm was used. In this case, the inner diameter of the main body of the rotating part was 15900 μm, and the diameter of the shaft part was 15600 μm. According to the stirring device according to the embodiment of the disclosed technology, the shear rate γ in the gap 37 is 1109 $s^{-1}$ from the start of the culture to the 10th day, and 1331 $s^{-1}$ after the 10th day. Furthermore, as a stirring device according to a comparative example, a stirring device which had no closing part and in which the dimension G of the gap 37 was 50 μm was used. In this case, the inner diameter of the main body of the rotating part was 15800 μm, and the diameter of the shaft part was 15700 μm. According to the stirring device according to the comparative example, the shear rate γ in the gap 37 is 3307 $s^{-1}$ from the start of the culture to the 10th day, and 3968 $s^{-1}$ after the 10th day.

TABLE 1

| | Closing part | Dimension G of gap | Shear rate γ |
|---|---|---|---|
| Example | Provided | 150 μm | Until day 10: 1109 $s^{-1}$<br>From day 10: 1331 $s^{-1}$ |
| Comparative Example | Not provided | 50 μm | Until day 10: 3307 $s^{-1}$<br>From day 10: 3968 $s^{-1}$ |

Figure 6A:
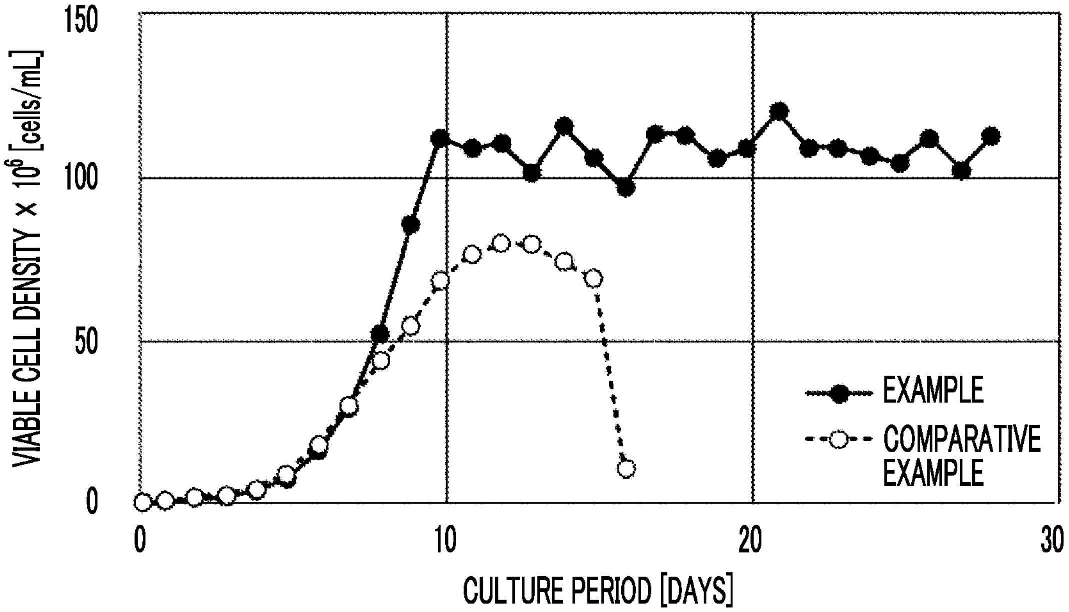
FIG. 6A is a graph showing transitions in viable cell density during a culture period.
Figure 6B:
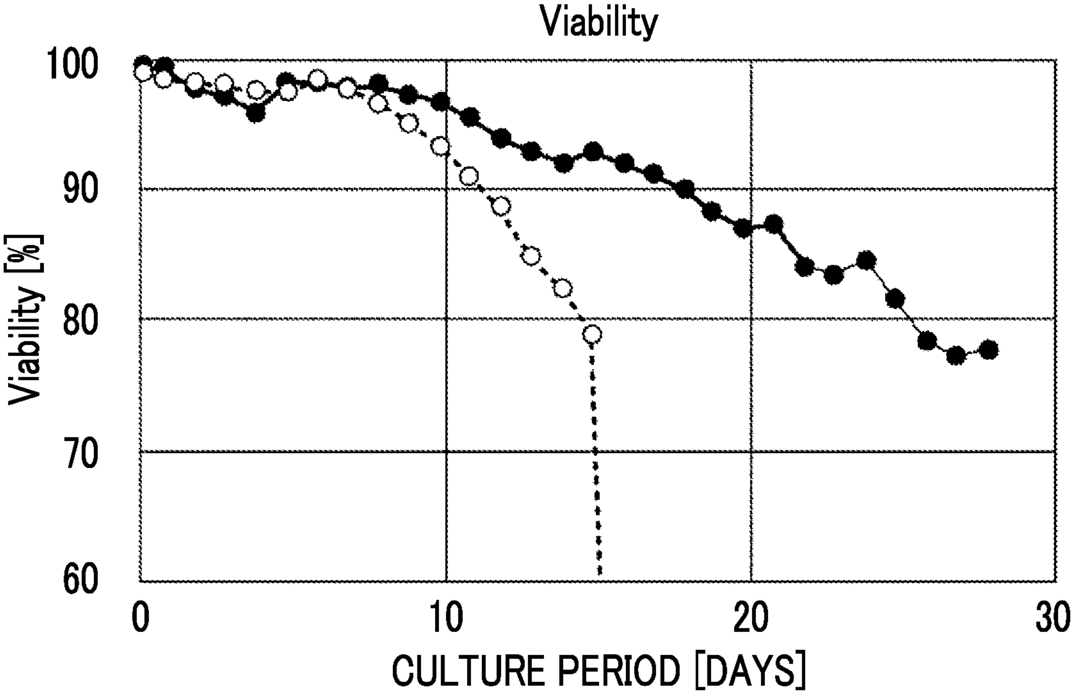
FIG. 6B is a graph showing transitions in cell viability during the culture period.

FIG. 6A is a graph showing transitions in viable cell density (VCD) during a culture period. FIG. 6B is a graph showing transitions in cell viability during the culture period. In a case where the stirring device according to the comparative example was used, the viable cell density and the cell viability decreased sharply on the 16th day after the start of the culture. On the other hand, in a case where the stirring device according to the embodiment of the disclosed technology was used, neither the viable cell density nor the cell viability decreased sharply. It is thought that this is because the inflow of the cell suspension into the gap 37 is inhibited by the closing part, and even in a case where the cells flow into the gap 37, the shear rate γ in the gap 37 is limited by the optimization of the dimension G of the gap 37, thereby restraining the damage to the cells.

The disclosure of Japanese Patent Application No. 2020-048440 filed on Mar. 18, 2020 is incorporated in the present specification by reference in its entirety. Furthermore, all publications, patent applications, and technical standards mentioned in this specification are herein incorporated by reference to the same extent as if each individual publication, patent application, or technical standard was specifically and individually indicated to be incorporated by reference.

What is claimed is:

1. A cell culture device comprising:
a culture vessel that accommodates a cell suspension containing cells and a culture medium; and
a stirring device that is provided at a bottom part of the culture vessel to stir the cell suspension accommodated in the culture vessel,
wherein the stirring device has
a shaft part,
a rotating part that has a hole part into which the shaft part is inserted, and is provided to have a gap of 100 μm or more between an interior wall demarcating the hole part and the shaft part so that the rotation part is rotatable with the shaft part as a rotation axis,
wherein a dimension of the gap is 400 μm or less, and
a closing part that closes an end part of the gap in an axial direction of the rotation axis.

2. The cell culture device according to claim 1,
wherein the closing part is provided at one end part of the gap in the axial direction of the rotation axis.

3. The cell culture device according to claim 1,
wherein the closing part is provided at both end parts of the gap in the axial direction of the rotation axis.

4. The cell culture device according to claim 1,
wherein the rotating part is rotated by a magnetic force.

5. The cell culture device according to claim 1,
wherein the closing part is configured to have a packing made of polymer.

6. The cell culture device according to claim 1,
wherein the culture vessel has the form of a bag.

7. The cell culture device according to claim 1, wherein a dimension of the gap is 150 μm or more and 400 μm or less.

8. A cell culture method which uses a cell culture device including:
a culture vessel that accommodates a cell suspension containing cells and a culture medium; and
a stirring device that is provided at a bottom part of the culture vessel to stir the cell suspension accommodated in the culture vessel,
wherein the stirring device has
a shaft part,
a rotating part that has a hole part into which the shaft part is inserted, and is provided to have a gap of 100 μm or more between an interior wall demarcating the hole part and the shaft part so that the rotation part is rotatable with the shaft part as a rotation axis,
wherein a dimension of the gap is 400 μm or less, and
a closing part that closes an end part of the gap in an axial direction of the rotation axis, the method comprising culturing cells while stirring a cell suspension accommodated in a culture vessel by rotation of a rotating part.

9. The cell culture method according to claim 8,
wherein the cells are cultured at a shear rate γ [$sec^{-1}$] defined by Equation (I) in a range of 200 $sec^{-1}$ or more and 3200 $sec^{-1}$ or less, in a case where a dimension of a gap is t [μm], and a rotation rate of the rotating part is s [m/sec], $$\gamma = s/t \times 10^{-6} \qquad (I).$$

10. The cell culture method according to claim 8,
wherein the cells are cultured by a perfusion culture scheme.

11. The cell culture method according to claim 8,
wherein the cells are cultured by a fed-batch scheme.

12. The cell culture method according to claim 8,
wherein the cells are CHO cells.

13. A production method of a product,
wherein a product is produced from cells cultured by a cell culture method which uses a cell culture device including:
a culture vessel that accommodates a cell suspension containing cells and a culture medium; and
a stirring device that is provided at a bottom part of the culture vessel to stir the cell suspension accommodated in the culture vessel,
wherein the stirring device has
a shaft part,
a rotating part that has a hole part into which the shaft part is inserted, and is provided to have a gap of 100 μm or more between an interior wall demarcating the hole part and the shaft part so that the rotation part is rotatable with the shaft part as a rotation axis, wherein a dimension of the gap is 400 μm or less, and a closing part that closes an end part of the gap in an axial direction of the rotation axis, the cell culture method including culturing cells while stirring a cell suspension accommodated in a culture vessel by rotation of a rotating part, the production method comprising a step of collecting a culture medium containing the product from the culture vessel.

14. The production method according to claim 13, wherein the product is an antibody.

* * * * *